United States Patent [19]
VanDeGraaf

[11] Patent Number: 6,068,821
[45] Date of Patent: May 30, 2000

[54] ELECTRONIC DEVICE HAVING A PROTECTIVE FRAMEWORK

[75] Inventor: Peter VanDeGraaf, Sevenum, Netherlands

[73] Assignee: 3M Innovative Properties Company, St. Paul, Minn.

[21] Appl. No.: 09/014,009

[22] Filed: Jan. 27, 1998

[30] Foreign Application Priority Data

Jan. 29, 1997 [GB] United Kingdom .................... 9701786

[51] Int. Cl.[7] ..................................................... A61L 2/20
[52] U.S. Cl. .............................. 422/300; 422/40; 422/99; 422/119; 422/292; 73/865.9; 248/603; 248/634; 206/521.2; 206/806; 206/822
[58] Field of Search ................................ 422/40, 99, 292, 422/297, 300, 119; 73/865.9; 248/693, 560, 603, 604, 610–612, 634, 635; 206/806, 822, 521, 521.2

[56] References Cited

U.S. PATENT DOCUMENTS

| 849,975 | 4/1907 | Carlson . |
| 2,696,322 | 12/1954 | Densen . |
| 2,854,049 | 9/1958 | Wyllie . |
| 3,129,836 | 4/1964 | Frevel . |
| 3,545,286 | 12/1970 | Stenstrom . |
| 3,592,422 | 7/1971 | Norman . |
| 4,860,507 | 8/1989 | Garza-Tamez ........................ 248/560 |
| 5,491,092 | 2/1996 | Colvin ...................................... 436/1 |
| 5,565,634 | 10/1996 | Graessle et al. ...................... 73/865.9 |

FOREIGN PATENT DOCUMENTS

| 0 485 071 | 5/1992 | European Pat. Off. . |
| 0 595 450 | 5/1994 | European Pat. Off. . |
| 1 511 692 | 5/1978 | United Kingdom . |
| 2 312 800 | 11/1997 | United Kingdom . |
| 93/21964 | 11/1993 | WIPO . |
| WO 98/33286 | 7/1998 | WIPO . |

Primary Examiner—Robert J. Warden, Sr.
Assistant Examiner—Fariborz Moazzam
Attorney, Agent, or Firm—Jeffrey J. Hohenshell

[57] ABSTRACT

An electronic device (1), for example a test pack for use in determining the efficacy of a sterilization cycle in a sterilizer, is provided with a protective framework (10) comprising two impact-absorbing ring-like members (11, 12) located on opposed sides of the device and three impact-absorbing arms (13) spaced apart from the device and extending at equispaced locations between the ring-like members.

16 Claims, 7 Drawing Sheets

ELECTRONIC DEVICE HAVING A PROTECTIVE FRAMEWORK

The present invention relates to a protective framework for an electronic device and, more especially, to a framework providing protection against impacts for an electronic device which is intended to be handled manually.

The invention is applicable, for example, to the protection of test packs or similar electronic devices which contain sensitive components, for example electronic sensors, and which are likely to be damaged if they are knocked or dropped while being handled. The invention is concerned especially, but not exclusively, with the protection of test packs for use in sterilization chambers for determining the efficacy of sterilization cycles.

A sterilization cycle in a sterilization chamber involves the use of a sterilant, for example steam, in combination with certain environmental conditions (for example elevated temperatures) to effect sterilization of items within the chamber. To ensure that a sterilizer is functioning correctly, the environmental conditions within the sterilization chamber should be monitored regularly and, to that end, test packs are available which are located in the sterilization chamber either alone or with items to be sterilized and, at the end of a sterilization cycle, indicate whether or not the cycle has been effective. Test packs which incorporate electronic components (for example, sensors for monitoring/measuring environmental conditions within the sterilization chamber) have been described and it is clearly desirable that a test pack of that type should be able to withstand impacts which it might receive while in use since any impact may damage the electronic components, with potentially serious consequences if the test pack then become unreliable. It is also desirable that such a test pack should be easy to handle and manipulate, even when it is hot following removal from a sterilization chamber.

The present invention is concerned with protecting an electronic device (especially, but not exclusively, a test pack for use in sterilizers) against damage by impacts, in a manner which does not unduly restrict user access to the device and which, preferably, facilitates the handling of the device.

The present invention provides an electronic device on which is mounted an external protective framework comprising two impact-absorbing ring-like members located on opposed sides of the device and at least three impact-absorbing arms, spaced apart from the device, which extend between the ring-like members at spaced locations around the device. The term "ring-like member" means a member which has the same general shape as a ring but is not necessary circular. It includes, for example, the case in which the member defines a closed figure such as a triangle, square or other straight-sided figure and, for the purposes of the present invention, is the equivalent of a ring.

A device in accordance with the invention may be a self-contained unit which can be located within a sterilization chamber for testing the efficacy of a sterilization cycle, in which case it may comprise a sterilant challenging path for challenging the penetration of sterilant from outside the unit to a predetermined location within the unit; electronic means operable, during said sterilization cycle, to determine whether or not sterilant has penetrated adequately to said predetermined location; and housing means for housing said sterilant challenge path and said electronic means, the protective framework being connected to the housing means of the device.

By way of example only, embodiments of the invention will be described with reference to the accompanying drawings, in which.

Figure 1:
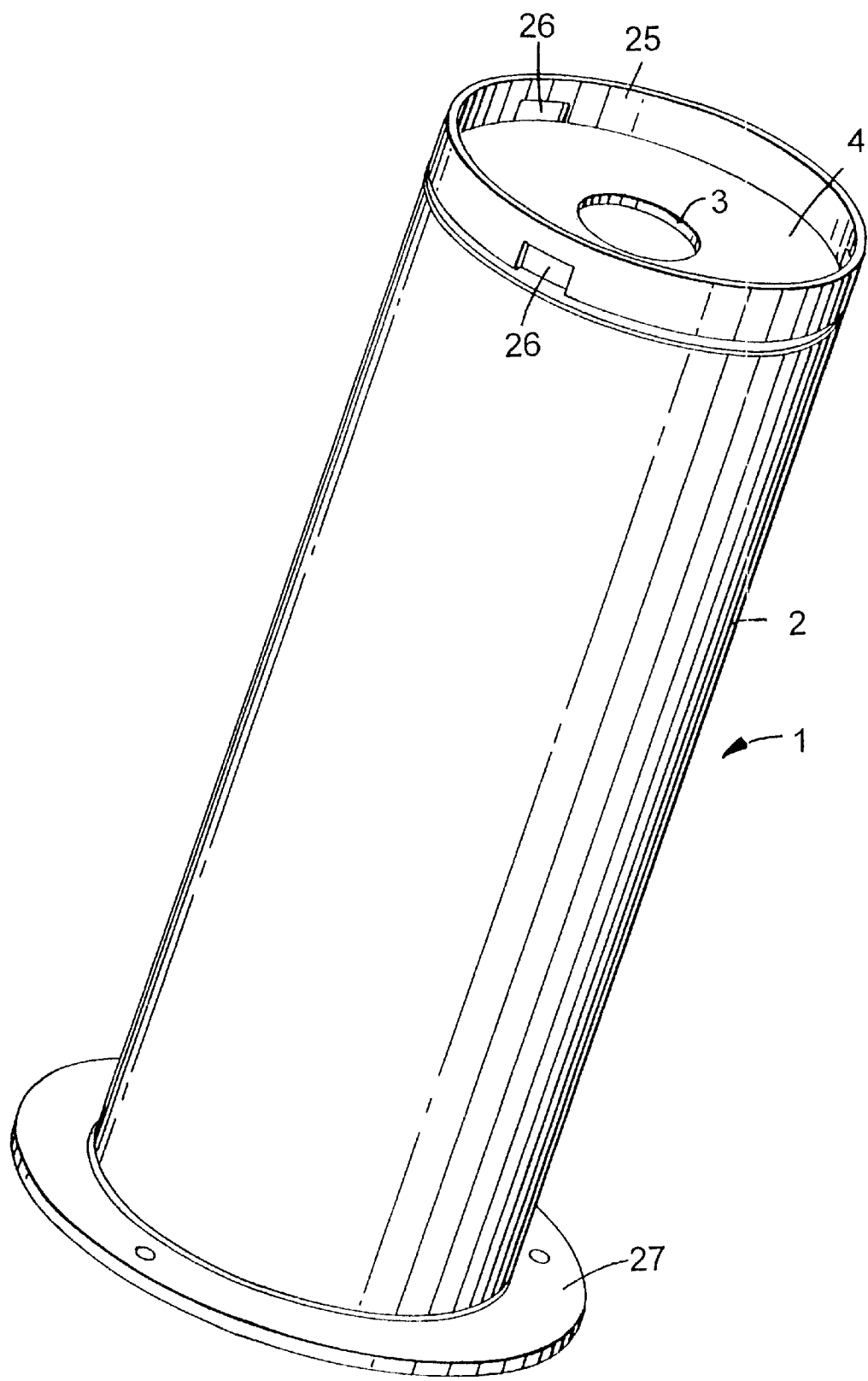
FIG. 1 is a perspective view of an electronic device.

The device 1 shown in FIG. 1 is a test pack for use in determining the efficacy of a sterilization cycle in the sterilization chamber of a porous-load sterilizer. The test pack is intended to be placed inside the sterilization chamber and to remain there throughout a sterilization cycle, during which time it monitors and records environmental conditions within the chamber so that, at the end of the cycle, a determination can be made as to whether or not the cycle was effective. The test pack has a cylindrical housing 2 within which are contained the components, including electronic components, necessary for the functioning of the device.

A detailed description of the method of operation and the internal construction of the test pack 1 are not essential for an understanding of the present invention but the test pack may, for example, incorporate some form of challenge load for challenging the penetration of sterilant through an opening (not visible) in the lower end of the housing 2 to a particular location within the housing. The sterilization cycle of a porous-load sterilizer typically commences with an air removal phase, to remove air from the sterilization chamber (including the load that is being sterilized) before the sterilant is applied, and the challenge load of the test pack 1 is so constructed that sterilant will be unable to reach the selected location within the housing 2 during a sterilization cycle unless that air removal phase has been effective. By providing sensors within the test pack for determining the presence/absence of sterilant at the selected location, the efficacy of the sterilization cycle can be determined. A test pack of that type, which uses temperature sensors to determine the penetration of sterilant within a challenge load, is described in U.S. Pat. No. 5,565,634. That document also describes how the test pack may include an electronic memory for recording the information from the temperature sensors, and a microprocessor for determining, on the basis of that information, if a sterilization cycle has been effective. U.S. Pat. No. 5,565,634 further describes how the test pack may give a visual indication, at the end of a sterilization cycle, of whether or not the cycle has been effective (e.g. through the use of an LED which will emit light to indicate that a cycle has been satisfactory) and also how recorded information about a sterilization cycle may be transferred, from the test pack to outside hardware, in the form of pulses of infrared radiation generated by an infrared LED within the test pack and transmitted through a window in the housing of the test pack. The housing 2 of the test pack 1 includes such a data transmission window, indicated by the reference 3, in its upper end face 4.

Figure 2:
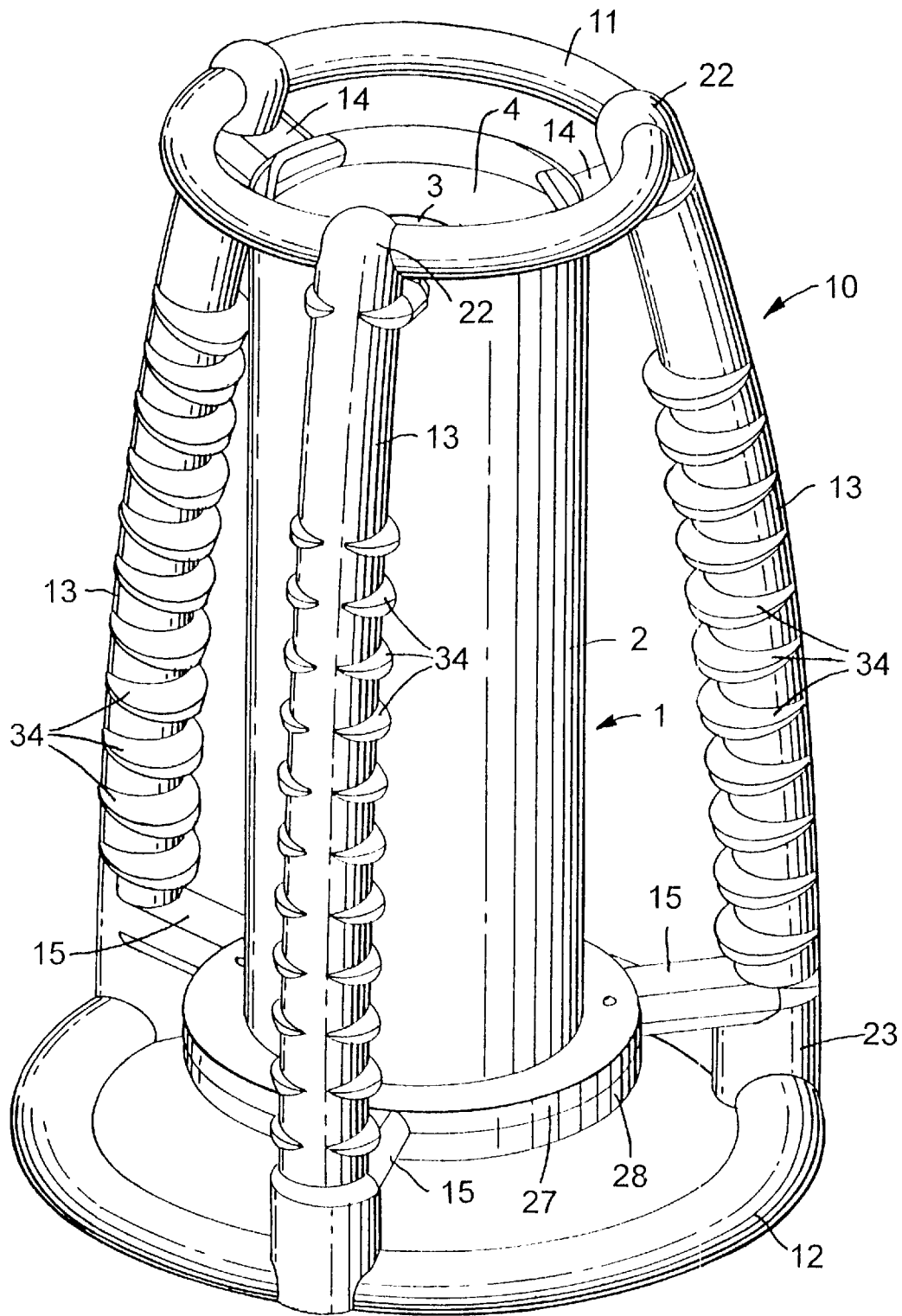
FIG. 2 is a perspective view of the device provided with a protective framework in accordance with the invention.

It will be appreciated that the test pack 1, despite the fact that it contains sensitive components, must be comparatively robust. It will be handled regularly, typically by the operators of sterilization equipment in a hospital, because it is essential that sterilizers are checked frequently to ensure that they are functioning effectively. To ensure the necessary degree of robustness and to facilitate the handling of the test pack, even when it is still hot after removal from a sterilizer, a protective framework 10 is provided which will now be described with reference to FIGS. 2 to 4.

The framework 10 comprises two rings 11, 12 and three arms 13. The ring 11 has a diameter slightly greater than the diameter of the cylindrical housing 2 and is located adjacent and slightly above the upper end of the test pack 1 (i.e. the end at which the data transmission window 3 is provided). The ring 12 is of larger diameter than the ring 11 and is located adjacent and slightly below the lower end of the test pack (i.e. the end in which the access opening to the sterilant challenge load is provided). The arms 13 extend between the rings 11, 12 at equi-spaced locations around the test pack and are bowed outwardly so that, throughout their length, they are spaced apart from the test pack housing 2. The framework 10 is mounted on the test pack by connecting members 14, 15 which extend inwards to the housing 2 from the upper and lower ends respectively of the arms 13.

The ring 12 at the lower end of the framework 10 provides a base on which the framework, and hence the test pack 1, can stand. The lower end of the test pack 1 is then located slightly above the supporting surface, as can be seen from FIG. 3, thus allowing access for sterilant to the challenge load opening in the lower end of the test pack. In addition, the data transmission window 3 in the upper end face 4 of the test pack is clearly visible through the center of the ring 11.

Each of the rings 11, 12 (shown partly broken away in FIG. 3) comprises an inner reinforcing member in the form of a solid core 16 of any material suitable for imparting sufficient rigidity and strength to the rings, for example a metal or rigid plastics material capable of withstanding the environmental conditions encountered in a sterilizer. Suitable materials for the cores 16 include stainless steel, aluminium, polyamide and PEEK (polyether ether ketone). Surrounding the core 16 of each ring is a softer, resilient material 17 also capable of withstanding the environmental conditions encountered in a sterilizer, for example silicone rubber. The resilient material 17 can be formed around the core 16 by, for example, an injection moulding process.

Each of the arms 13 also comprises an inner reinforcing member for imparting sufficient rigidity and strength to the arm but, in this case, the reinforcing member is a bowed tube 18 of a material capable of withstanding the environmental conditions encountered in a sterilizer. The tubes 18, like the cores 16 of the rings 11, 12, may be of metal or rigid plastics material and suitable materials include stainless steel, aluminium, polyamide and PEEK (polyether ether ketone). Each tube 18 is flattened at each end and bent through 90°, to form the cores 19, 20 of the connecting members 14, 15 respectively. In addition, the end of the flattened core 19 at the upper end of each arm 13 is turned upwards as indicated at 22 in FIG. 3, for connection to the test pack 1 as described below. The tube 18, and the flattened ends 19, 20 are surrounded by a softer, resilient material 21 (preferably the same material as that used in the rings 11, 12) which is extended at each end of the tubes 18 to form portions 22, 23 with no inner reinforcement, in which the upper and lower rings 11, 12 are located as will be described below. The portion 23 of resilient material at the lower end of each arm 13 has a flattened end surface 24 on which the framework 10 can stand as already described. The resilient material 21, including the extended portions 22, 23 can be formed around each of the tubes 18 by, for example, an injection molding process.

The use of tubular material for the reinforcement 18 of the arms 13 allows the arms to be formed with a larger diameter without increasing the weight of the framework 10. The larger diameter of the arms 13 is desirable because, as described below, they function also as handles and should have a diameter which allows them to be held comfortably.

The use of the extended portions 22, 23 of the arms 13 to provide the location points for the rings 11, 12 is advantageous because it results in the reinforcement cores 16 and tubes 18 being separated from one another by the resilient material 21 and further enhances the ability of the framework 10 to absorb impacts.

To mount the framework 10 on the test pack 1, the arms 13 are first connected to the test pack and the rings 11, 12 are then connected to the arms as will be described below.

Figure 3:
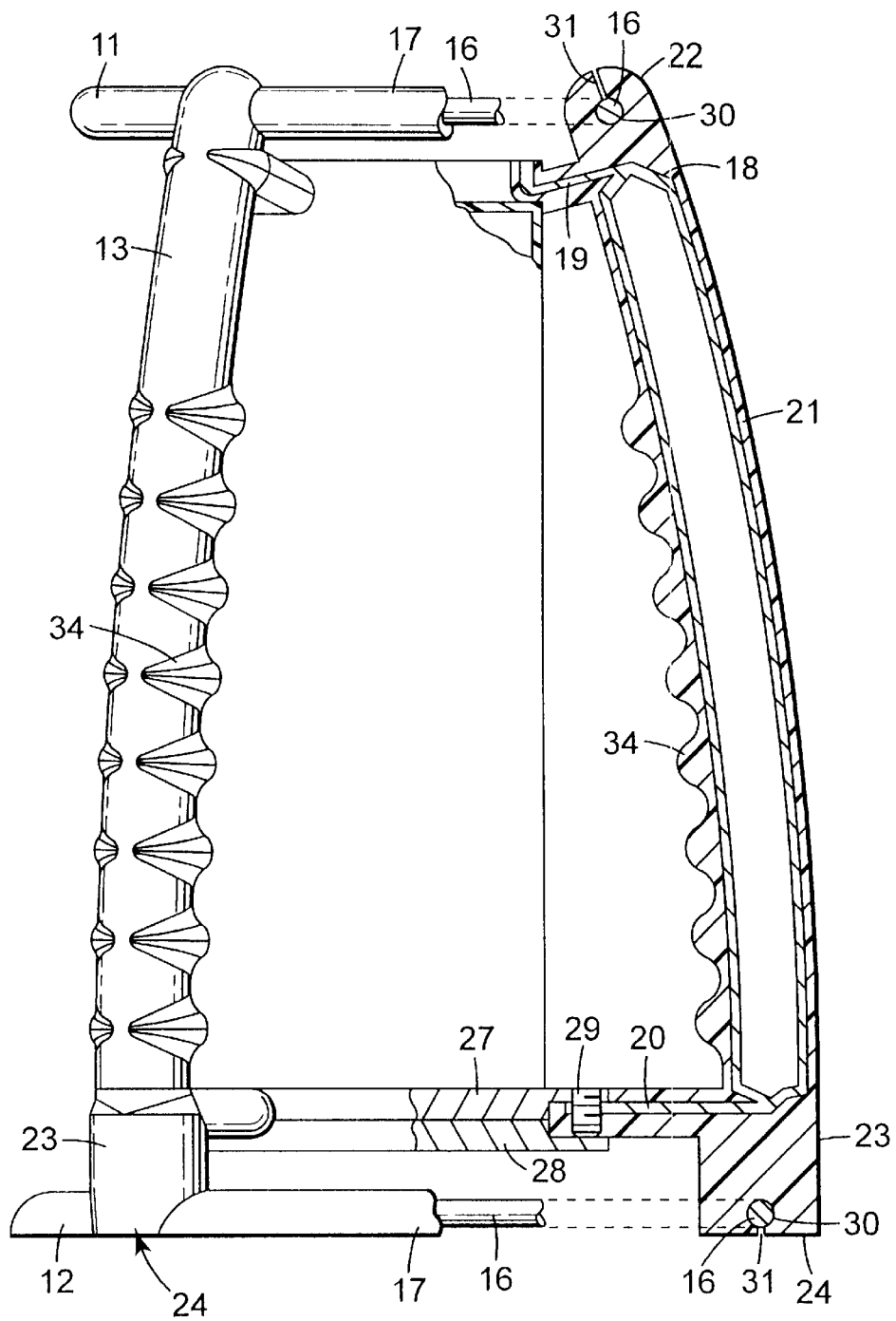
FIG. 3 is a side view of the device shown in FIG. 2, partly in cross-section and partly broken away.
Figure 4:
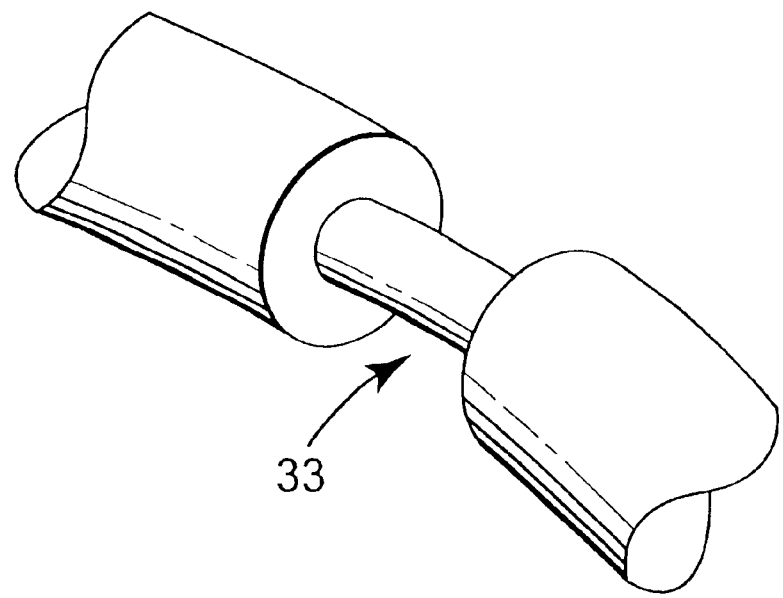
FIG. 4 is a perspective view of parts of two components of the framework of FIG. 2, prior to assembly.
Figure 4:
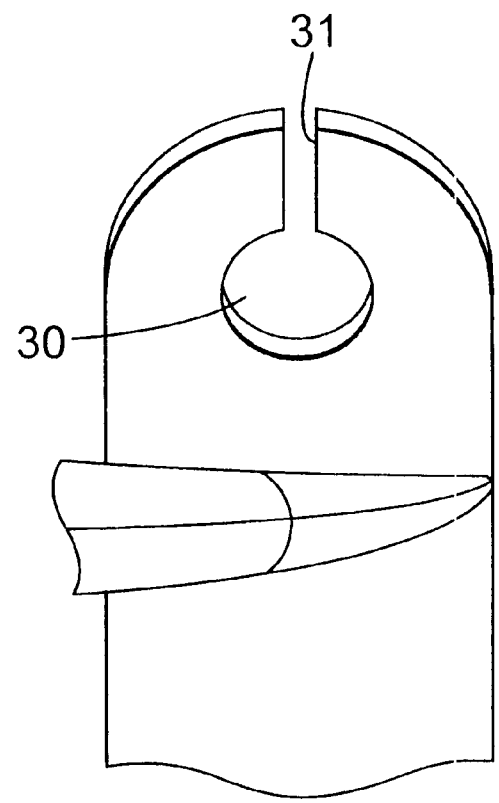

To enable the arms 13 to be connected to the test pack 1, the latter is provided at its upper end with an upstanding collar 25 formed with apertures 26 into which the upturned ends 22 of the connecting members 14 of the arms are hooked as shown in FIG. 3. The lower end of the test pack is provided with a pair of end plates 27, 28 between which the connecting members 15 of the arms are clamped, as is also shown in FIG. 3. The end plates 27, 28 (only one of which is shown on the test pack 1 in FIG. 1) are held together by screws 29 which also pass through the connecting members 15.

To enable the rings 11, 12 to be connected to the arms 13, the latter are formed adjacent each end (in the portions 22, 23) with transversely-extending apertures 30 (FIGS. 3 and 4) having a diameter corresponding to that of the core 16 of the rings. Slits 31 at the ends of the arms, in the resilient material 21, provide a means of entry into the apertures 30. In addition, each ring 11, 12 is formed with three equi-spaced breaks 33 in the resilient material 17 so that, at these locations, the core 16 of the ring is exposed (see FIG. 4). To connect a ring 11, 12 to an arm 13, the breaks 33 in the resilient material on the ring are positioned adjacent the ends of respective arms 13 and pressed into the apertures 30 through the slits 31.

The framework 10 formed as described above is a rigid and strong construction, completely covered by the resilient material 17, 21. The framework is spaced from, and forms a buffer zone around, the test pack 1 and will take up and absorb impacts which might otherwise damage components within the test pack. The framework 10 also provides a stand for the test pack 1 as already described, and the shape of the framework acts as a visual indication to the user of the correct orientation of the test pack. In particular, the shape of the framework indicates that it should be stood on the broad base provided by the ends 23 of the arms 13, rather than on the ends 22 or on the curved sides of the arms (the curvature of the latter serving, in fact, to suggest instability). In addition, the arms 13 provide a particularly convenient way of handling the test pack, enabling it not only to be picked up (with two hands when necessary) but also to be passed easily from one hand to another and from one user to another. To provide additional security when the test pack is being handled, the resilient material 21 covering the arms is shaped to provide grip portions 34. Because the resilient material 21 has a comparatively low thermal conductivity, the grip portions 34 will remain comparatively cool for the user to handle even if the test pack is hot following removal from a sterilization chamber.

Typically, the test pack 1 has a diameter of about 80 mm and a height of about 240 mm. In a suitable protective framework 10 for a test pack having those dimensions, the rings 11, 12 have outer diameters of about 110 mm and 190 mm respectively. The cores 16 of the rings have a diameter of about 8 mm and the resilient material 17 has a thickness of about 2 mm. The reinforcing tubes 18 in the arms have an outer diameter of about 16 mm and the resilient material 21 (ignoring the grip portions 34) has a thickness of about 2 mm. The overall height of the framework 10 is about 280 mm.

Figure 5:
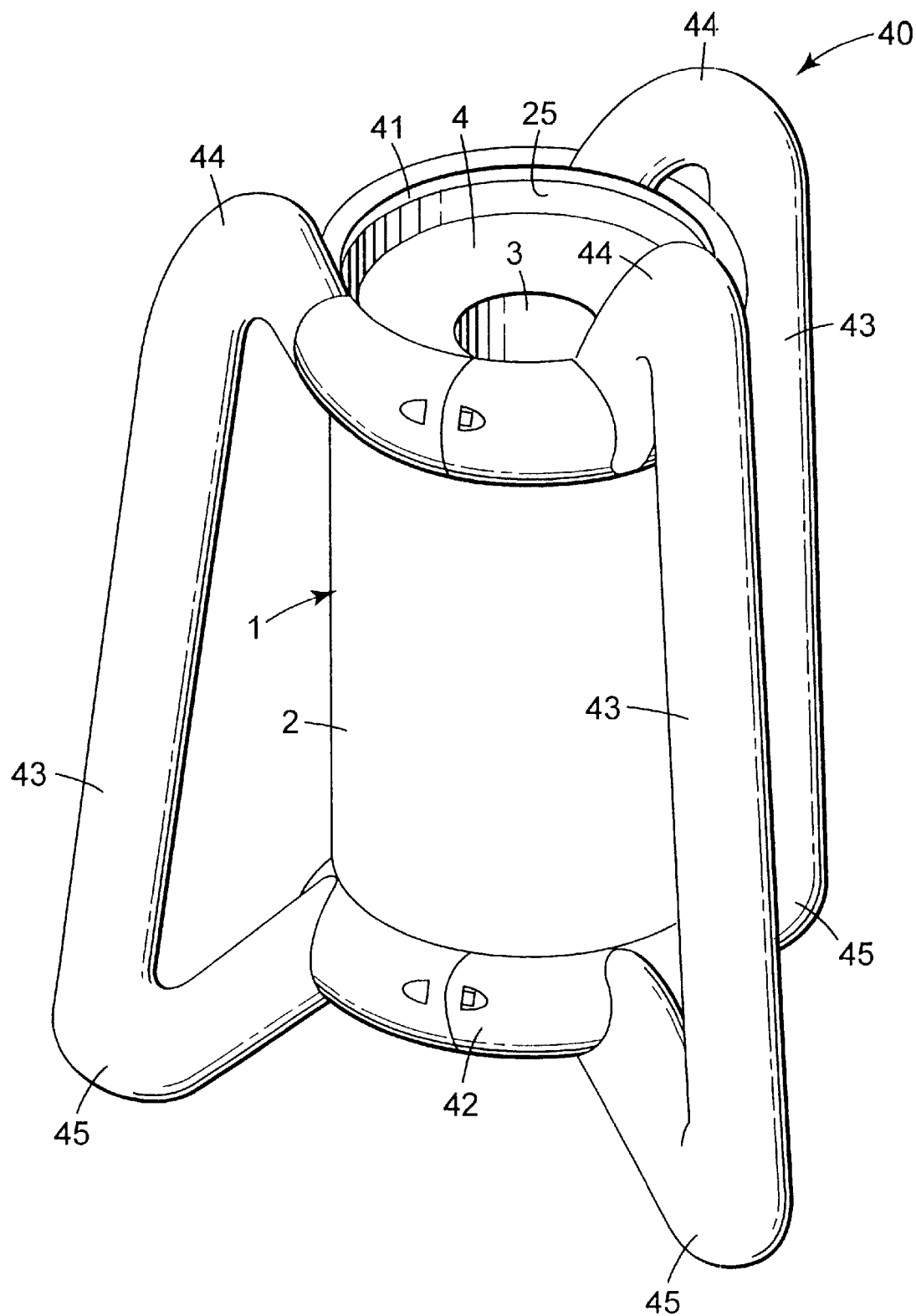
FIG. 5 is a view similar to FIG. 2 but showing an alternative protective framework.

An alternative form of protective framework for the test pack 1 is illustrated in FIG. 5. The framework 40 is similar to that of FIG. 2 in that it also comprises two rings 41, 42 located adjacent respective ends of the cylindrical test pack 1, and three arms 43 which extend between the rings 41, 42 at equi-spaced locations. In this case, however, the test pack is seated directly in the rings 41, 42 and the arms 43, instead of being bowed outwardly, are shaped adjacent their ends as indicated at 44, 45 to space them apart from the test pack housing 2.

Figure 6:
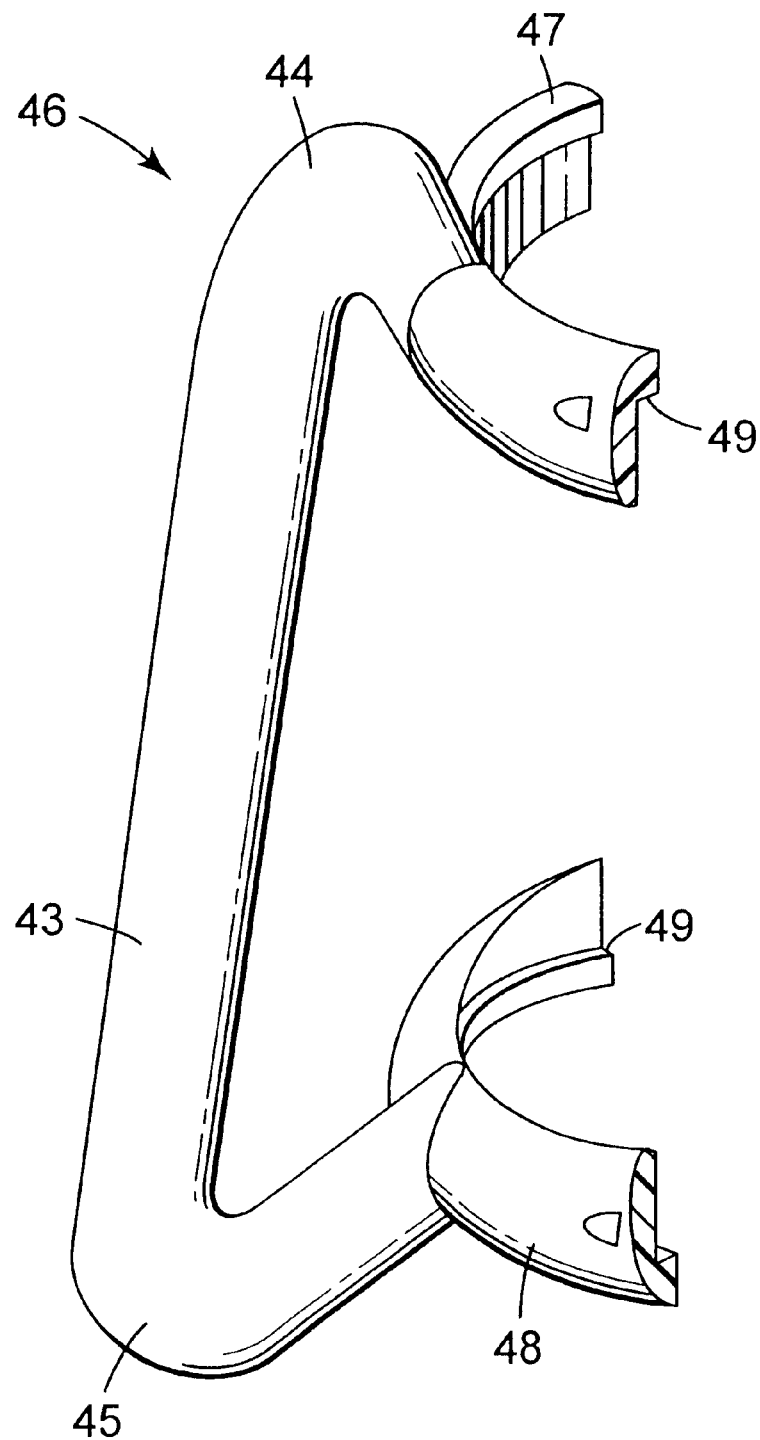
FIG. 6 is a perspective view of one component of the framework of FIG. 5, prior to assembly.
Figure 7:
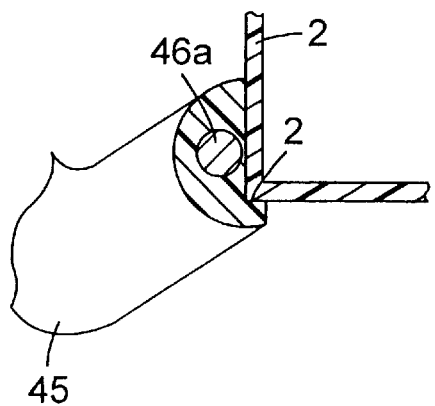
FIG. 7 is a detail view, partly in cross-section, of part of the framework of FIG. 5.
Figure 8:
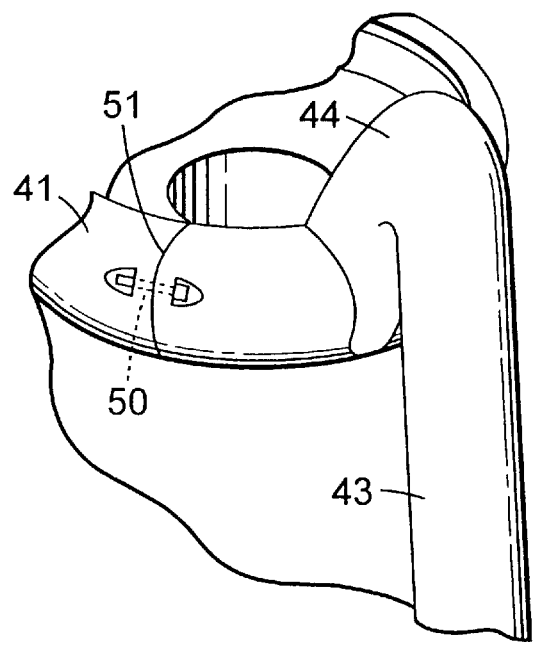
FIG. 8 is a detail view of another part of the framework of FIG. 5.

The framework 40 may be formed in three parts 46, each comprising one arm 43 and a section 47, 48 of each of the rings 41, 42 as illustrated in FIG. 6. Each part 46 may comprise a comparatively rigid core 46a surrounded by a softer resilient material, both capable of withstanding the environmental conditions encountered in a sterilizer. The internal surfaces of the ring sections 47, 48 are shaped to provide a ledge 49 (FIG. 7) on which the respective end of the test pack is located and, when all three frame parts 46 are in position on the test pack, adjacent frame parts are secured together by screws 50 inserted tangentially into the rings 41, 42 across the junctions 51 between adjacent ring sections 47, 48 as illustrated in FIG. 8.

The shaped lower end portions 45 of the arms 43 form a stand for the framework 40 and, hence, for the test pack 1. The arms 43 extend generally outwards, away from the test pack 1, towards the bottom of the framework 40 and thus provide a visual indication to the user of the correct orientation of the test pack (i.e. that it should be stood on the broader base provided by the ends 45 of the arms 43). The lower end of the test pack 1 is then located slightly above the supporting surface, as can be seen from FIG. 5, thus allowing access for sterilant to the challenge load opening in the lower end of the test pack. In addition, the data transmission window 3 in the upper end face 4 of the test pack is clearly visible through the center of the upper ring 41 of the framework.

The framework 40 formed as described above is a rigid and strong construction, completely covered by a resilient material and, like the framework 10, forms a buffer zone around the test pack 1 and will take up and absorb impacts which might otherwise damage components within the test pack. The arms 43, like the arms 13 of the framework 10, enable the test pack to be picked up easily and to be passed without difficulty from one hand to another and from one user to another and, by virtue of the covering of resilient material, will remain comparatively cool even if the test pack is still hot following removal from a sterilization chamber. If desired, the resilient material covering the arms 43 may be shaped to provide grip portions similar to the grip portions 34 of FIG. 2.

It will be appreciated that, although the frameworks 10, 40 have been described as applied to a test pack for use in sterilization chambers, they could be applied to other devices which require similar protection. The general positioning of the framework relative to the device to be protected should take account of which parts of the device are required to be accessible to the user, either visually (like the data transmission window 3 of the test pack 1) or manually, since such access is conveniently provided through the centre of one or both of the rings 11, 12, 41. 42. The device to be protected need not be cylindrical, in which case the overall shape of the framework should be modified to provide an appropriate buffer zone around the device: the framework may, for example be provided with more than three arms 13, 43 and the rings 11, 12, 41, 42 need not be circular but could, for example, have a generally triangular, rectangular, or other, geometry.

I claim:

1. A self-contained device for determining the adequacy of a sterilization cycle comprising:

a substantially cylindrical test pack having a first end and a second end, said test pack including electronic components for determining the adequacy of a sterilization cycle; and a protective framework situated external of said test pack, said protective framework comprising:

a first impact-absorbing, ring-like member substantially adjacent said first end of said test pack, a second impact-absorbing, ring-like member substantially adjacent said second end of said test pack; and at least three impact absorbing arms at least partially spaced from said test pack, each of said impact absorbing arms extending from said first ring-like member to said second ring-like member.

2. A device according to claim 1 wherein said first ring-like member is smaller than said second ring-like member.

3. A device according to claim 1 wherein said second ring-like member is sized and shaped to form a base upon which the device can stand.

4. A device according to claim 1, wherein said arms extend between the first and second ring-like members at substantially equi-spaced locations on said first and second ring-like members.

5. A device according to claim 1 wherein the test pack is seated in the first and second ring-like members.

6. A device according to claim 1 wherein the first and second ring-like members are substantially circular.

7. A device according to claim 1, wherein the arms and the first and second ring-like members comprise a strengthening member encased in a resilient material.

8. A device according to claim 7, wherein the strengthening member comprises a metal material.

9. A device according to claim 7, wherein the strengthening member comprises a plastic material.

10. A device according to claim 7, wherein the resilient material comprises an elastomeric material.

11. A device according to claim 1, wherein the arms are sized and shaped to be manually grasped by a user.

12. A device according to claim 1, wherein the substantially cylindrical test pack has an imaginary axis, and said arms extend axially beyond the ends of the test pack.

13. A device according to claim 1, wherein the arms have ends and the first and second ring-like members have structures that are sized and shaped to receive the ends of the arms.

14. A device according to claim 1, wherein the arms have ends and said arms are bowed outwardly between ends.

15. A device according to claim 1, wherein the test pack comprises electronic means operable, during the sterilization cycle, to determine whether sterilant has penetrated adequately into a predetermined location within the test pack; and housing means for housing said electronic means.

16. A device according to claim 15, wherein the housing means includes a window through which information can be transmitted from within the test pack, the window being accessible through substantially a center of one of the ring-like members.

* * * * *